US005739020A

United States Patent [19]

Pope

[11] Patent Number: 5,739,020
[45] Date of Patent: *Apr. 14, 1998

[54] ENCAPSULATION OF ANIMAL AND MICROBIAL CELLS IN AN INORGANIC GEL PREPARED FROM AN ORGANOSILICON

[76] Inventor: Edward J. A. Pope, 447 Lorenzo Dr., Agoura, Calif. 91301

[*] Notice: The term of this patent shall not extend beyond the expiration date of Pat. No. 5,693,513.

[21] Appl. No.: 371,064

[22] Filed: Jan. 10, 1995

[51] Int. Cl.⁶ .............................. C12N 11/14; C12N 5/00; C12N 11/04; C12Q 1/02
[52] U.S. Cl. .................. 435/176; 424/93.7; 435/29; 435/182; 435/382
[58] Field of Search ................. 424/93.7; 435/176, 435/177, 182, 29, 382

[56] References Cited

U.S. PATENT DOCUMENTS

| | | | |
|---|---|---|---|
| 4,148,689 | 4/1979 | Hino et al. | 435/176 |
| 4,391,909 | 7/1983 | Lim | 435/178 |
| 4,797,213 | 1/1989 | Parisius | 210/651 |
| 5,192,549 | 3/1993 | Barenolz et al. | 424/450 |
| 5,200,334 | 4/1993 | Dunn et al. | 435/182 |

Primary Examiner—David M. Naff
Attorney, Agent, or Firm—W. Edward Johansen

[57] ABSTRACT

Living animal tissue cells and microbial cells such as yeast cells are encapsulated in an inorganic gel prepared from an organosilicon. Encapsulation of tissue cells is performed by mixing an organosilicon precursor with a highly acidic aqueous solution to hydrolyze the organosilicon precursor and provide a gel forming solution, cooling the gel forming solution, forming a mixture of living tissue cells and Hank's balanced salt solution, adding a base solution to the gel forming solution, immediately thereafter adding the mixture containing tissue cells to the gel forming solution, and pouring the resultant mixture into a container where an inorganic gel forms encapsulating the tissue cells. The organosilicon precursor may be tetraethoxysilane, tetrabutoxysilane, tetramethoxysilane or tetrapropoxysilane. Microbial cells are encapsulated by a similar procedure where a gel forming solution is prepared by adding a base to a solution resulting from hydrolyzing an organosilicon with a highly acidic aqueous solution, a microbial cell dispersion is mixed with the gel forming solution and the resultant mixture is poured into a container to form an inorganic gel encapsulating the microbial cells.

2 Claims, No Drawings

ENCAPSULATION OF ANIMAL AND MICROBIAL CELLS IN AN INORGANIC GEL PREPARED FROM AN ORGANOSILICON

BACKGROUND OF THE INVENTION

The field of the invention is sol-gel encapsulation of living animal tissue cells and living micro-organism.

The following patents and textual material are hereby incorporated by reference into the specification.

U.S. Pat. No. 4,983,369 a process for producing highly uniform microspheres of silica having an average diameter of 0.1–10 microns from the hydrolysis of a silica precursor, such as tetraalkoxysilanes, which is characterized by employing precursor solutions and feed rates which initially yield a two-phase reaction mixture.

U.S. Pat. No. 4,943,425 teaches a method of making high purity, dense silica of large particles size. Tetraethylorthosilicate is mixed with ethanol and is added to a dilute acid solution having a pH of about 2.25. The resulting solution is digested for about 5 hours, then 2N ammonium hydroxide is added to form a gel at a pH of 8.5. The gel is screened through an 18–20 mesh screen, vacuum baked, calcined in an oxygen atmosphere and finally heated to about 1200° C. in air to form a large particle size, high purity, dense silica.

U.S. Pat. No. 5,200,334 teaches an active biological material in a glass which is formed using a sol-gel process. A metal alkoxide is mixed with water and exposed to ultrasonic energy at a ph=<2 to form a single phase solution which is buffered to a pH between about 5 and 7. The buffered solution is then mixed with the active biological material and the resultant gel is aged and dried. The dried products is a transparent porous glass with substantially all of the added active biological material encapsualted therein the biolgical material retaining a high level of activity.

U.S. Pat. No. 5,292,801 teaches a method of obtaining a chemical interaction between at least one reagent trapped in sol-gel glass by doping it with a reagent, and diffusable solutes or components in an adjacent liquid or gas phase. The reagents, the solutes or the components can be any organic or inorganic compounds or materials of biologically orgin including enzymes. The doped sol-gel glass in various forms may be useful as an analytical test, chromatographic medium, sensor, catalyst or biocatalyst, electrode or enzyme electrode or other detection device.

U.S. Pat. No. 5,290,692 teaches a fibrininolytic enzyme such as urikinase, tissue plasminogen activator or streptokinase is covalently bounded to a bioadaptable porous crystalline glass to produce a thrombolytic material. Production of the glass involves combining 40–50 mol % calcium oxide, 20–30 mol % titanium dioxide and 25–35 mol % diphosphorous pentoxide to form a mixture, and combining the mixture with 0.5–4.0 mol % disodium oxide. A bioreactor for converting plasminogen in blood into plasmin can be prepared by packing the material in a column. When finely comminuted, the material can be administered into the blood of a patient for removing blood clots.

U.S. Pat. No. 4,138,292 teaches an enzyme or microorganism which is entrapped within the gel matrix of a sulfated polysaccharide in the presence of ammonium ion, a metal ion, a water-soluble amine or a water-miscible organic solvent. The polysaccharide contains more than 10 w/w % of a sulfate moiety in its molecule. The immobilized enzyme or microorganism thus obtained shows a high level of catalytic activity for a long period of time and can be used for continuous enzymatic reactions with substrates.

U.S. Pat. No. 4,251,387 teaches techniques for producing semipermeable microcapsules by interfacial polymerization. The material to be encapsulated and a hydrophilic monomer are emulsified within a hydrophobic continuous phase. Polymerization is initiated by dissolving a second monomer in the continuous phase, and occurs only at the interface of the emulsion to result in the formation of macroporous, poorly defined capsule membranes. Next, the affinity of the continuous phase for the hydrophilic monomer is varied by altering the polarity of the continuous phase. This step is accomplished either by isolating and resuspending the raw phase of different polar character, or by mixing a second solvent with the continuous phase. By controlling the affinity and the concentration of the second monomer, it is possible to produce microcapsules having uniform capsule membranes and a selected upper limit of permeability.

U.S. Pat. No. 4,246,349 teaches bacteria which are immobilized by adsorption on an inorganic carrier which are stabilized by carrying out the adsorption procedure in the presence of from about 1 to about 20% weight per volume of sucrose of nonfat dry milk solids and lyophilizing the adsorbed bacteria.

U.S. Pat. No. 4,391,909 teaches tissue cells such as islet of Langerhans cells or liver cells which are encapsulated within a spheroidal semipermeable membrane including a polysaccharide having acidic groups cross-linked with a polymer having a molecular weight greater than 3,000. The cells within the microcapsules are viable, healthy, physiologically active and capable of ongoing metabolism. The encapsulated cells are useful for implantation in a mammalian body to produce substances and effect chemical changes characteristic of the cells in vivo tissue.

U.S. Pat. No. 4,438,198 a biochemically active matrix for use in a bio-artificial organ which has an enzyme covalently bonded to a matrix of organochemically cross-linked fibrin. The matrix may be suspended in a medium of agarose which irreversibly solidifies below 37° C. The bio-artificial organ is useful for extracorporeal treatment of blood to remove excess substrate from the blood.

SUMMARY OF INVENTION

The present invention is generally directed to a process for synthesizing sol-gels which encapsulate an active biological material.

In a first separate aspect of the present invention, the active biological material is living animal tissue cells.

In a second separate aspect of the present invention, the active biological material is living micro-organisms.

Other aspects and many of the attendant advantages will be more readily appreciated as the same becomes better understood by reference to the following detailed description.

The features of the present invention which are believed to be novel are set forth with particularity in the appended claims.

DESCRIPTION OF THE PREFERRED EMBODIMENT

A process for synthesizing a sol-gel encapsulating an active biological material includes the steps of placing into a first container an organosilicon precursor and a highly acidic solution having a molar concentration in the range of 0.05 to 2.5 to form an immiscible solution, stirring the immiscible solution until the immiscible solution becomes clear, chilling the clear immiscible solution in an ice bath, placing into a second container living animal tissue cells and a salt solution to form a tissue solution. In an embodiment the living animal tissue cells are from beef liver (bovine hepatocytes). There is a standard procedure for dispersing living animal tissue cells. The beef liver is cut into small cubes. About 10 grams of the small cubes of beef liver are placed in 60 milliliters of Hank's basic salt solution (also known as Hank's Balanced Salt Solution) for one half hour in order to remove the hemoglobin from the beef lever. The Hank's basic salt solution is removed. Forty milligrams of collagenase and sixty milligrams of dispase are dissolved in the Hank's basic salt solution. Dispase and collagenase are enzymes. The Hank's basic salt solution is shaken for one half hour and decanted to form a tissue solution. The tissue solution is a supernatent solution which has individual living liver cells dispersed therein.

The process also includes the steps of adding a base solution having a molar concentration in the range of 0.05 to 2.5 to the clear immiscible solution, immediately thereafter adding the tissue solution to the clear immiscible solution and the base solution, stirring the clear immiscible solution, the base solution and the tissue solution to form a gel forming solution and casting the gel forming solution into a test tube to form a sol-gel encapsulating the tissue cells of an animal.

The organosilicon precursor is an selected from a group consisting of tetraethoxysilane (TEOS), tetrabutoxysilane (TBOS), tetramethoxysilane (TMOS) and tetrapropoxysilane (TPOS). Other organometellic include aluminum tri (sec)butoxide and zirconium isopropoxide. The highly acidic solution is selected from a group consisting of nitric acid ($HNO_3$) and hydrochloric acid (HCl). Other highly acidic solutions may also be used including sulfuric acide ($H_2SO_4$). In the preferred embodiment the base solution is ammonium hydroxide. Please refer to C. J. Brinker. *Journal of Non-Crystaline Solutions*, Volume 48, page 48 and Volume 63, page 45.

The tissue cells of an animal may be harvested from the liver, the pancreas, the thyroid, the parathyroid, the pituitary gland and the renal cortex of mammels including man. The sol-gel which encapsulates one of these tissue cells may be used in an artificial organ such as either an artificial liver or an artificial pancreas.

Sol-gel is a versatile technique for making silica ceramics with porosity ranging from a few percent to as high as 99 percent. Because sol-gel are made under mild process conditions a variety of delicate materials may be incorporated into the sol-gel. The process for incorporating cells into a gel involves three basic steps: staining the cells to follow their geometric distribution with the gel, forming the gel and monitoring cell metabolism. *Saccharomyces cerevesiae* cells, brewer's yeast, are an ideal model organism for Gel Encapsulated Microorganisms. The yeast cells are stained with 8-hydroxy-1, 3,6 trisulfonated pyrene trisodium salt (pyranine). The pyranine dyes are used as molecular probes for water content, pH changes in phospholipid vesicles, and the chemical processes in aluminoslicate sols and gels. Pronated pyranine, which exists at low-pH, shows a strong blue luminescence when excited by radiation at 430 nanometers while the depronated pyranine, which exists at high-pH, fluoresces at 515 nanometers when excited by radiation at 365 nanometers. Alcohol/water ratios can be followed by measuring the relative luminescence/fluorsecence at the two wavelengths.

Another process for synthesizing a sol-gel encapsulating an active biological material includes the steps of placing into a container an organosilicon precursor from a group consisting of tetraethoxysilane (TEOS), tetrabutoxysilane (TBOS), tetramethoxysilane (TMOS) and tetrapropoxysilane (TPOS), and a highly acidic solution from a group consisting of nitric acid ($HNO_3$) and hydrochloric acid (HCl) having a molar concentration in the range of 0.05 to 2.5 and stirring the organosilicon precursor and the highly acidic solution whereby water in the highly acidic solution hydrolizes the organosilicon precursor. The process also includes the steps of adding a base solution having a molar concentration in the range of 0.05 to 2.5 from a group consisting of ammonium hydroxide and stirring the organosilicon precursor, the highly acidic solution and the base solution. The process further includes the steps of adding a prestained *Saccharomyces cerevesiae* dispersion and stirring the organosilicon precursor, the highly acidic solution, the base solution and the prestained *Saccharomyces cerevesiae* dispersion to form a gel forming solution. The gel forming solution is cast into a test tube to form a gel.

In an experiment tetraethoxysilane (TEOS) and hydrochloric acid (HCl) having a molar concentration of 0.1 were placed into a container to form a turbid mixture. After one half hour the turbid mixture becomes clear because of hydrolysis of the tetraethoxysilane and the evolution of ethanol. Ammonium hydroxide having a molar concentration of 0.1 is added to neutralize the clear mixture and then a stained yeast dispersion (suspension) is introduced into the neutralized clear mixture. After the yeast cells are mixed in, portions of the sol-gel are poured into polyethylene tubes and stored at 5 degrees C. Gels appear beige under normal illumination and fluoresce bright green at 365 nanometers. The average pore size for the matrix is 10 nanometers and the average size of the yeast cells is about 10 microns. The yeast cells are essentially "shrink-wrapped" inside the silicon-oxygen-silicon matrix. Pore size is sufficient for nutrients to reach the cells on all sides, but the pores are much smaller than the yeast cells themselves. The size difference between pore size and cell size—a factor of 1000—illustrate the gentleness of the sol-gel process. The yeast cells are not lysed and continue to function after the matrix closes in around them.

From the foregoing it can be seen that a sol-gel encapsulating an active biological materials, including tissue cells of an animal and micro-organisms, has been described. Accordingly it is intended that the foregoing disclosure shall be considered only as an illustration of the principle of the present invention.

What is claimed is:

1. A process for encapsulating living animal tissue cells in an inorganic gel comprising the steps of:

a. mixing an organosilicon precursor and a highly acidic aqueous solution having a molar concentration of acid in the range of 0.05 to 2.5 to form a gel forming solution wherein said organosilicon precursor is selected from a group consisting of tetraethoxysilane, tetrabutoxysilane, tetramethoxysilane and tetrapropoxysilane;

b. stirring said gel forming solution until said gel forming solution becomes clear whereby water in said highly acidic aqueous solution hydrolyzes said organosilicon precursor;

c. chilling said gel forming solution in an ice bath;

d. mixing living animal tissue cells and Hanks' Balanced Salt Solution to form a solution containing said living animal tissue cells;

e. adding a base solution having a molar concentration of base in the range of 0.05 to 2.5 to said gel forming solution;

f. immediately thereafter adding the solution containing living animal tissue resulting from step d to the gel forming solution resulting from step e to form a mixture of said solution containing living animal tissue cells and said gel forming solution;

g. stirring the mixture from step f; and h. pouring into a container the mixture from step g to form an inorganic gel encapsulating said living animal tissue cells.

2. A process encapsulating microorganisms in an inorganic gel comprising the steps of:

a. mixing an organosilicon precursor and a highly acidic aqueous solution having a molar concentration of acid in the range of 0.05 to 2.5 wherein said organosilicon precursor is selected from a group consisting of tetraethoxysilane, tetrabutoxysilane, tetramethoxysilane and tetrapropoxysilane;

b. stirring said mixture of said organosilicon precursor and said highly acidic aqueous solution until said mixture of said organosilicon precursor and said highly aqueous acidic solution becomes clear whereby water in said highly aqueous acidic solution hydrolyzes said organosilicon precursor;

c. adding a base solution having a molar concentration of base in the range of 0.05 to 2.5 to said mixture of said organosilicon precursor and said highly acidic aqueous solution to form a mixture of said organosilicon precursor, said highly acidic aqueous solution and said base solution;

d. stirring said mixture of said organosilicon precursor, said highly acidic solution and said base solution to form a gel forming solution;

e. mixing a microorganism dispersion with said gel forming solution to form a mixture of said microorganism dispersion and said gel forming solution; and f. pouring into a container said mixture of said microorganism dispersion and said gel forming solution to form an inorganic gel encapsulating said microorganisms.

* * * * *